(12) United States Patent
Landgrebe et al.

(10) Patent No.: US 12,329,874 B2
(45) Date of Patent: Jun. 17, 2025

(54) ACTIVATOR SYSTEM FOR BIOLOGICAL INDICATOR

(71) Applicant: Solventum Intellectual Properties Company, Maplewood, MN (US)

(72) Inventors: Kevin D. Landgrebe, Woodbury, MN (US); G. Marco Bommarito, Stillwater, MN (US); Wensheng Xia, Woodbury, MN (US); Timothy A. Kohman, Cottage Grove, MN (US); Timothy J. Nies, Stillwater, MN (US); Nicholas R. Powley, St. Paul, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 1032 days.

(21) Appl. No.: 17/309,502

(22) PCT Filed: Dec. 19, 2019

(86) PCT No.: PCT/IB2019/061113
§ 371 (c)(1),
(2) Date: Jun. 2, 2021

(87) PCT Pub. No.: WO2020/128959
PCT Pub. Date: Jun. 25, 2020

(65) Prior Publication Data
US 2022/0031900 A1 Feb. 3, 2022

Related U.S. Application Data

(60) Provisional application No. 62/783,708, filed on Dec. 21, 2018.

(51) Int. Cl.
| *A61L 2/28* | (2006.01) |
| *G01N 21/77* | (2006.01) |
| *G01N 21/78* | (2006.01) |

(52) U.S. Cl.
CPC ............ *A61L 2/28* (2013.01); *A61L 2202/122* (2013.01); *A61L 2202/14* (2013.01); *G01N 21/77* (2013.01); *G01N 21/78* (2013.01)

(58) Field of Classification Search
CPC .. A61L 2/28; A61L 2202/122; A61L 2202/14; G01N 21/77; G01N 21/78; G01N 21/80
(Continued)

(56) References Cited

U.S. PATENT DOCUMENTS

| 4,353,990 A | 10/1982 | Manske et al. |
| 5,073,488 A | 12/1991 | Matner |

(Continued)

FOREIGN PATENT DOCUMENTS

| EP | 2341946 | 7/2011 |
| EP | 3074523 | 10/2016 |

(Continued)

OTHER PUBLICATIONS

International Search report for PCT International Application No. PCT/IB2019/061113 mailed on Apr. 6, 2020, 5 pages.

*Primary Examiner* — Maureen Wallenhorst (57) ABSTRACT

A system for assessing efficacy of a sterilization process is disclosed. The system includes a biological indicator, a receptacle configured to receive the biological indicator, an actuator mechanism, and a sensing system operatively coupled to the actuator mechanism. A method of using the system for assessing efficacy of a sterilization process is also disclosed.

16 Claims, 6 Drawing Sheets

(58) Field of Classification Search
USPC .... 422/400, 401, 402, 405, 408, 413, 82.08,
422/547; 436/164, 165, 172
See application file for complete search history.

(56) References Cited

U.S. PATENT DOCUMENTS

| | | | | |
|---|---|---|---|---|
| 5,167,923 | A | * | 12/1992 | Van Iperen ............... A61L 2/28 435/31 |
| 5,418,167 | A | | 5/1995 | Matner |
| 5,552,320 | A | | 9/1996 | Smith |
| 5,736,355 | A | | 4/1998 | Dyke |
| 5,830,683 | A | | 11/1998 | Hendricks et al. |
| 6,623,955 | B2 | | 9/2003 | Matner |
| 6,924,139 | B2 | | 8/2005 | Eveland |
| 8,173,388 | B2 | | 5/2012 | Pasmore |
| 2005/0014214 | A1 | * | 1/2005 | Eveland ................. C12Q 1/04 435/29 |
| 2010/0081165 | A1 | | 4/2010 | Pasmore et al. |
| 2011/0182770 | A1 | | 7/2011 | Chandrapati |
| 2013/0217107 | A1 | * | 8/2013 | Pederson ................ C12Q 1/22 435/287.4 |
| 2015/0374868 | A1 | * | 12/2015 | Bruce .................... A61L 2/208 422/119 |
| 2016/0263264 | A1 | | 9/2016 | Schulz et al. |
| 2017/0000919 | A1 | * | 1/2017 | Childers ............... G01L 9/0072 |
| 2017/0037447 | A1 | | 2/2017 | Chandrapati |
| 2019/0017091 | A1 | * | 1/2019 | Centanni ................. C12Q 1/22 |
| 2020/0179550 | A1 | * | 6/2020 | Fang ........................ A61L 2/28 |
| 2022/0296741 | A1 | * | 9/2022 | Henniges ............... G01K 11/06 |

FOREIGN PATENT DOCUMENTS

| | | |
|---|---|---|
| JP | S56145993 | 4/1981 |
| JP | 56145993 | 11/1981 |
| JP | S57150964 A | 9/1982 |
| JP | 2004222957 A | 8/2004 |
| JP | 2012503994 A | 2/2012 |
| JP | 2013530723 A | 8/2013 |
| JP | 2017501757 A | 1/2017 |
| WO | WO 2009-151886 | 12/2009 |
| WO | 2010039388 A2 | 4/2010 |
| WO | 2012012055 A2 | 1/2012 |
| WO | WO 2017-131872 | 8/2017 |

* cited by examiner

ACTIVATOR SYSTEM FOR BIOLOGICAL INDICATOR

CROSS REFERENCE TO RELATED APPLICATIONS

This application is a national stage filing under 35 U.S.C. 371 of PCT/IB2019/061113, filed Dec. 19, 2019, which claims the benefit of U.S. Provisional Application No. 62/783,708 filed Dec. 21, 2018, the disclosure of which is incorporated by reference in its/their entirety herein.

BACKGROUND

Medical instruments, particularly surgical instruments, are typically sterilized prior to use using steam or other sterilizing gases or liquids. A commonly used sterilization process is exposure of the instruments to steam under pressure. Alternative sterilization processes use gasses such as ethylene oxide and hydrogen peroxide as the sterilant.

Sterilization indicators are used to monitor whether a sterilization process has been performed and/or whether critical sterilization parameters have been met. Sterilization chemical indicators, which assess exposure to the chemical constituent used in the sterilization process, e.g., steam, ethylene oxide, hydrogen peroxide, etc., include a chemical-indicating composition, carried on a substrate, which changes color during the sterilization process. Sterilization biological indicators, which contain a population of viable microorganisms, such as a population of bacterial spores, show whether the sterilization process has killed all of the spores present in the biological indicator.

In typical use, a biological indicator is placed within the sterilizer, either as is, or as part of a test pack. Subsequently, the sterilization cycle is conducted, and then the biological indicator is removed from the sterilizer and placed into an incubator for a specified period of time. The incubator may contain a reader, which typically detects fluorescence of a molecule whose non-fluorescent precursor can be metabolized and converted to the fluorescent molecule by spores. Alternatively, biological indicators may be visually assessed by observation of the color of the detection medium of the biological indicator, which typically changes color in the presence of actively metabolizing germinated spores due to change in color of a pH indicator that is present in the detection medium. While detection of fluorescence from a suitably-designed biological indicator can typically indicate whether spores are dead or alive in a shorter time than is required for the appearance of a color change of a pH indicator in a biological indicator, there is still a time lag between the end of a sterilization cycle and assessment of the state of the biological indicator. In some extreme cases, the need for the instruments that were sterilized during the sterilization cycle arises before the biological indicator is ready to be read. In these extreme instances, not having a rapid means for providing an assessment of the sterilization conditions to which the instruments that are to be used on a patient were subjected presents a risk that unsterilized instruments could unknowingly be used on a patient. Thus, there is a need for biological indicators that can be read immediately upon removal of the biological indicator from the sterilizer. Thus, since biological indicators must be incubated so that any viable bacterial spores comprised by the indicator can begin to grow and form metabolites that result in a fluorescent signal or a change in color of detection medium, there is a need for the ability to incubate biological indicators while they are inside the sterilizer. The present disclosure provides a biological indicator activation system that enables activation of a biological indicator during the post-exposure phase of a sterilization cycle, and thus provides a biological indicator that can be read essentially as soon as the indicator is removed from the sterilizer.

SUMMARY

Generally, the present disclosure relates to activator systems. More particularly, the present disclosure relates to activator systems useful for activating biological indicators used for monitoring sterilization processes. Advantageously, the system can activate the biological indicator while the indicator is disposed in a sterilizer after the system has been exposed to a sterilization process in the sterilizer but before the sterilizer has been opened to remove the biological indicator.

In one aspect, the present disclosure provides a system for assessing efficacy of a sterilization process. The system can comprise a biological indicator, a receptacle configured to receive the biological indicator, an actuator mechanism, and a sensing system operatively coupled to the actuator mechanism. In any embodiment, the biological indicator can comprise a source of biological activity disposed therein. In any of the above embodiments, the biological indicator can comprise an activatable reservoir. In any of the above embodiments, the activatable reservoir can contain therein an indicator for detecting the biological activity. In certain embodiments, the actuator mechanism can contain therein an indicator for detecting the biological activity. In any of the above embodiments, the actuator mechanism can comprise a part that is configured to move from a first position to a second position. In any of the above embodiments, the sensing system can be capable of sensing a parameter selected from the group consisting of pressure, temperature, time, and a combination of any two or more of the foregoing parameters. In certain embodiments, the sensing system can comprise a temperature-reactive chemical. In certain embodiments, the temperature-reactive chemical can have a melting point that is greater than 100° C. In certain embodiments, the sensing system can be capable of being electrically or electronically connected to a sterilizer.

In another aspect, the present disclosure provides a device. The device can be used in a method of assessing efficacy of a sterilization process. The device can comprise a receptacle that defines a compartment dimensioned to receive a biological indicator, an actuator mechanism, and a sensing system operatively coupled to the actuator mechanism. In any of the above embodiments, the actuator mechanism can comprise a part that is configured to move from a first position to a second position. In certain embodiments, the actuator mechanism can contain therein an indicator for detecting the biological activity. In any of the above embodiments, the sensing system can sense a parameter selected from the group consisting of pressure, temperature, time, and a combination of any two or more of the foregoing parameters. In certain embodiments, the sensing system can comprise a temperature-reactive chemical. In certain embodiments, the temperature-reactive chemical can have a melting point that is greater than 100° C. In certain embodiments, the sensing system can be capable of being electrically or electronically connected to a sterilizer.

In yet another aspect, the present disclosure provides a method. The method can be used to determine efficacy of a sterilization process. The method can comprise placing a device into a sterilization chamber of a sterilizer; wherein the device comprises a receptacle that defines a compartment dimensioned to receive a biological indicator, an actuator mechanism, and a sensing system operatively coupled to the actuator mechanism; wherein the biological indicator is disposed in the compartment. The method further can comprise, while the device with the biological indicator disposed therein is disposed in the sterilization chamber, operating the sterilizer to expose the device and the biological indicator to a sterilant. The method further can comprise, after exposing the device and the biological indicator to the sterilant but before unsealing the sterilization chamber, activating the biological indicator.

All scientific and technical terms used herein have meanings commonly used in the art unless otherwise specified. The definitions provided herein are to facilitate understanding of certain terms used frequently in this application and are not meant to exclude a reasonable interpretation of those terms in the context of the present disclosure.

Unless otherwise indicated, all numbers in the description and the claims expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

The recitation of numerical ranges by endpoints includes all numbers subsumed within that range (e.g. a range from 1 to 5 includes, for instance, 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The term "biological indicator" as used herein refers to an article containing a source of biological activity (e.g., a test microorganism or an enzyme having enzymatic activity) and optional detection medium (comprising nutrients for growing the test microorganisms and/or detection reagent(s) for detecting the source of biological activity) that can be used to monitor the efficacy of a sterilization process by detection of inactivation, or lack thereof, of the source of biological activity.

The term "activate" as used herein in the context of a biological indicator refers to the action of causing the contacting of detection medium with a source of biological activity, including mixing. In some embodiments, a frangible container comprising the detection medium is crushed to activate the biological indicator.

The term "receptacle" as used herein refers to a holder for a biological indicator. In some embodiments, the receptacle comprises a narrowed lumen that challenges the entry of sterilant into the receptacle and into the biological indicator. In some embodiments, the receptacle contains an actuator mechanism and a sensing system.

The term "actuator mechanism" as used herein refers to a mechanical feature (e.g., a piston, a septum, etc.) that accomplishes, carries out, or initiates the process of, activation of the biological indicator. In some embodiments, the actuator mechanism comprises a piston that moves longitudinally or radially to compress the biological indicator longitudinally or radially; the movement of the piston causes a detection medium-comprising vial of the biological indicator to break, thus allowing detection medium to combine with a source of biological activity (e.g., bacterial spores). In some embodiments, the actuator mechanism comprises one or more of the following: a chemical actuator, a mechanical actuator, and an electrical actuator, or combinations thereof. In some embodiments, the chemical actuator, the mechanical actuator, and the electrical actuator power the piston or the septum of the actuator mechanism and, ultimately, cause activation of the biological indicator by acting on the piston or septum to compress the biological indicator.

The term "sensing system" as used herein refers to a system that senses conditions (e.g., pressure, temperature, time) of the sterilization process. The sensing system senses conditions of the sterilization process and ensures that the activator system activates the biological indicator at the appropriate time. In some embodiments, the sensing system comprises a solid that expands upon melting over a specific temperature range. In some embodiments, the sensing system is an electronic temperature sensor or electronic pressure sensor that causes an actuator mechanism to activate the biological indicator. In some embodiments, the sensing system is electrically or electronically connected, including by wireless connection, to the sterilizer, so that sensors within the sterilizer can be used to inform the sensing system of the activator system of conditions within the sterilizer and, thus, to the appropriate time for the biological indicator to be activated.

The term "frangible" as used herein refers, in the context of a container, to any container that can be acted upon to release its contents, for example, by breaking it, puncturing it, shattering it, cutting it, bending it, etc.

BRIEF DESCRIPTION OF THE DRAWINGS

FIGS. 7A-B are sequential cross-sectional side views of the activator device of FIG. 6A with a biological indicator disposed therein, wherein FIG. 7A shows the device and biological indicator before activation and FIG. 7B shows the device and biological indicator after activation.

FIGS. 8A-B are sequential cross-sectional side views of an alternative embodiment of an activator device with a biological indicator disposed therein, wherein FIG. 8A shows the device and biological indicator before activation and FIG. 8B shows the device and biological indicator after activation.

In the following description, reference is made to the accompanying figures herein described. In certain cases, the figures may depict, by way of illustration, several specific embodiments of the present disclosure. It is to be understood that other embodiments different from those explicitly depicted in the figures are contemplated and may be made without departing from the scope or spirit of the present disclosure. The following detailed description, therefore, is not to be taken in a limiting sense.

DETAILED DESCRIPTION

Figure 1:
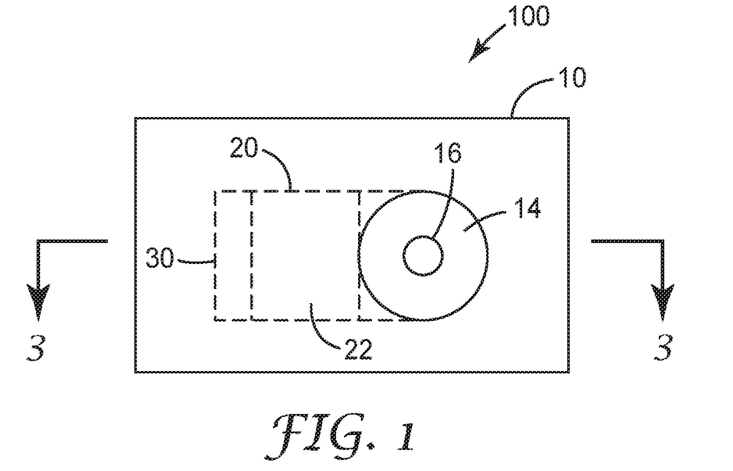
FIG. 1 is a plan view of one embodiment of a device for activating a biological indicator according to the present disclosure.
Figure 2:
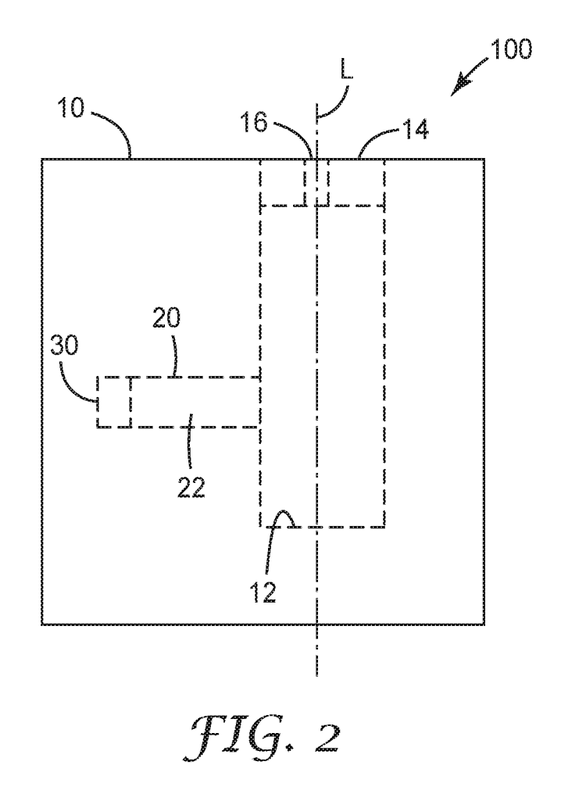
FIG. 2 is a side view of the device of FIG. 1.
Figure 3:
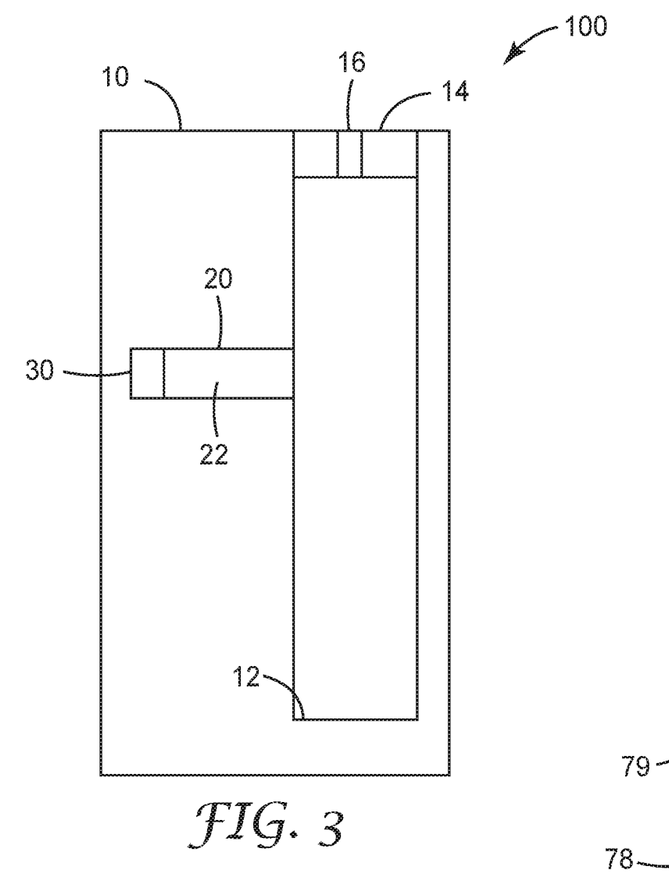
FIG. 3 is a cross-sectional side view, along line 3-3, of the device of FIG. 1.

Referring now to the drawings, FIGS. 1-3 show various views of an embodiment of the activator device 100 of the present disclosure. An embodiment of the activator device 100 of the present disclosure contains a receptacle 10 for a biological indicator 70, an actuator mechanism 20, and a sensing system 30 operatively coupled to the actuator mechanism 20. The receptacle 10 comprises a compartment 12 configured (e.g., shaped and/or dimensioned) to receive a biological indicator. The compartment 12 has a longitudinal axis L. The compartment 12 is in fluid communication with the ambient environment (e.g., the atmosphere) outside the receptacle 10. In some embodiments, the activator device 100 further comprises a plug 14. The plug can comprise a vent 16 that allows a sterilant, such as steam, hydrogen peroxide, ethylene oxide, etc., to permeate the compartment 12 of the receptacle 10 and a biological indicator (not shown in FIGS. 1-3) disposed therein. In some embodiments, the sensing system 30 is a chemical, such as a wax 32, which expands on heating. In some embodiments, the actuator mechanism 20 of the present disclosure comprises a part (e.g., piston 22) that is configured to move from a first position to a second position in response to a force (e.g., a force generated by expansion of a wax 32 as it is heated and changes from a solid to a liquid state). When the piston 22 moves from the first position to the second position, it thereby compresses and activates a biological indicator (not shown in FIGS. 1-3) disposed in the compartment 12 of the activator device 100. Thus, in some embodiments, the second position of the part (piston 22) of the actuator mechanism 20 places at least a portion of the part in a volume defined by the compartment 12 of the receptacle 10.

In any embodiment, the biological indicator used in the activator device 100 of the present disclosure can be a self-contained biological indicator. Non-limiting examples of biological indicators include the biological indicators described in U.S. Pat. Nos. 8,173,388; 6,924,139; 5,736,355; 5,552,320; 6,623,955; and 5,418,167.

Figure 4A:
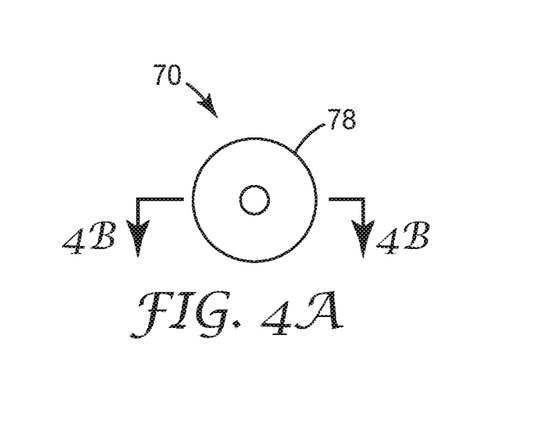
FIG. 4A is a top view of one embodiment of a biological indicator for use in an activator system of the present disclosure.
Figure 4B:
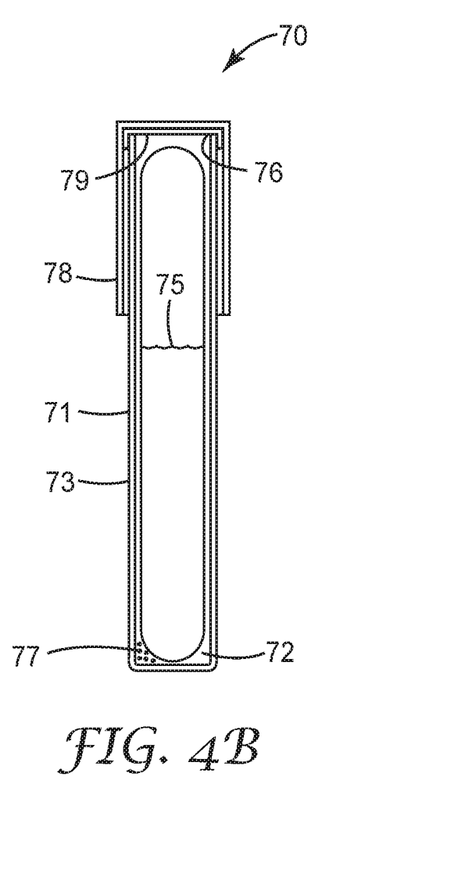
FIG. 4B is a cross-sectional side view, along line 4B-4B, of the biological indicator of FIG. 4A.

FIGS. 4A-B show various views of one embodiment of a biological indicator 70 suitable for use in the activator system of the present disclosure. Known biological sterilization process indicator constructions such as those described in U.S. Pat. No. 5,073,488 (Matner et al.) may be used with an activator system of the present disclosure. Other indicator constructions may also be used, such as those described in U.S. Patent Application Publication No. US 2017/0037447 (Chandrapati et al.), filed Oct. 17, 2008, entitled Biological Sterilization Indicator, System, and Methods of Using Same.

An embodiment of a biological indicator 70 suitable for use in an activator system of the present disclosure includes a housing 71 having an open chamber 72 defined by at least one gas and liquid impermeable wall 73. Alternative embodiments for these structures are shown in U.S. Patent Application Publication No. US 2017/0037447. The housing 71 is shown as a circular tube, but other known configurations can be used. In some embodiments, the at least one wall 73 is preferably transparent or translucent to the extent that a fluorescence intensity at a particular wavelength can be measured. Suitable materials for the walls may include glass, polycarbonate, polypropylene, polyester, and the like. For certain embodiments, the at least one wall 73 of the housing transmits at least 90% of incident light within a wavelength range of at least 500 to 700 nm, preferably at least 500 to 675 nm. The biological indicator comprises a source of biological activity (e.g., an enzyme and/or a test microorganism) disposed therein. In the illustrated embodiment of FIG. 4B, the open chamber 72 contains the source of biological activity (i.e., a predetermined number of viable sterilization process resistant test microorganisms 77 (e.g., spores)). Optionally, the source of biological activity (e.g., test microorganisms) may be disposed on a carrier (not shown) such as a paper or plastic strip, for example.

In any embodiment, the biological indicator 70 may include a sealed reservoir. In some embodiments, the sealed reservoir (e.g., container 74) may hold a detection medium 75. In some embodiments, the sealed reservoir may hold the source of biological activity. The container 74 holding the detection medium 75 is shown within open cavity 72 of the biological indicator 70. Alternatively (not shown), sealed reservoir can be positioned outside of and adjacent the cavity (e.g., as a portion of the actuator mechanism as described herein). The container 74, which is sealed, can be a breakable ampoule, but could alternatively be a container equipped with a plug, or other mechanism which, when activated, allows detection medium 75 to contact the test microorganisms 77. Container 74 is shown as an elongated ampoule, but other known configurations can be used as well.

The detection medium 75 comprises a detection reagent for detecting the source of biological activity. Detection reagents for detecting a source of biological activity in a biological indicator are well known in the art and include, for example, fluorogenic enzyme substrates, chromogenic enzyme substrates, and fermentable carbohydrates in combination with a pH indicator. In certain embodiments, the detection medium comprises a solvent (e.g., sterile water) that is suitable for dissolving and/or suspending the detection reagent and the source of biological activity in order to facilitate detection of the biological activity.

Optionally, a portion of wall 73 may be used as carrier on which the test microorganisms 77 are disposed (e.g., as a coating). An opening 76 to cavity 72 is provided with a gas-transmissive, microorganism-impermeable closure member 79, which may be adhered to housing 71 by an adhesive, a heat seal, or the like. Alternatively, closure member may be held on to opening 76 with a cap 78 having an aperture to permit sterilant to pass through. During exposure to a sterilant (e.g., during a sterilization process), the sterilant passes through the closure member 79, enters cavity 72, and contacts the test microorganisms 77. Alternative embodiments for these structures are shown in U.S. Patent Application Publication No. US 2017/0037447.

Figure 5A:
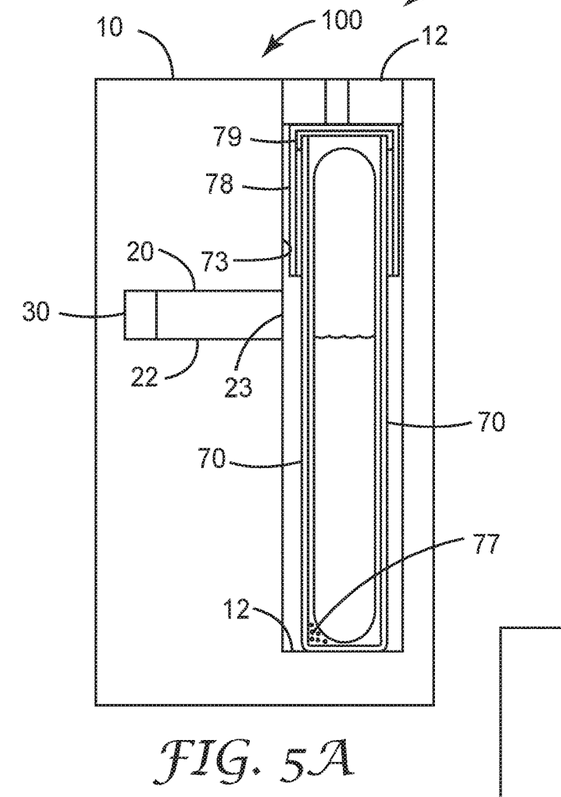
FIGS. 5A-B are cross-sectional side views of one embodiment of an activator system according to the present disclosure, wherein the activator system comprises a part of an actuator, the part being capable of moving from a first position to a second position.
Figure 5B:
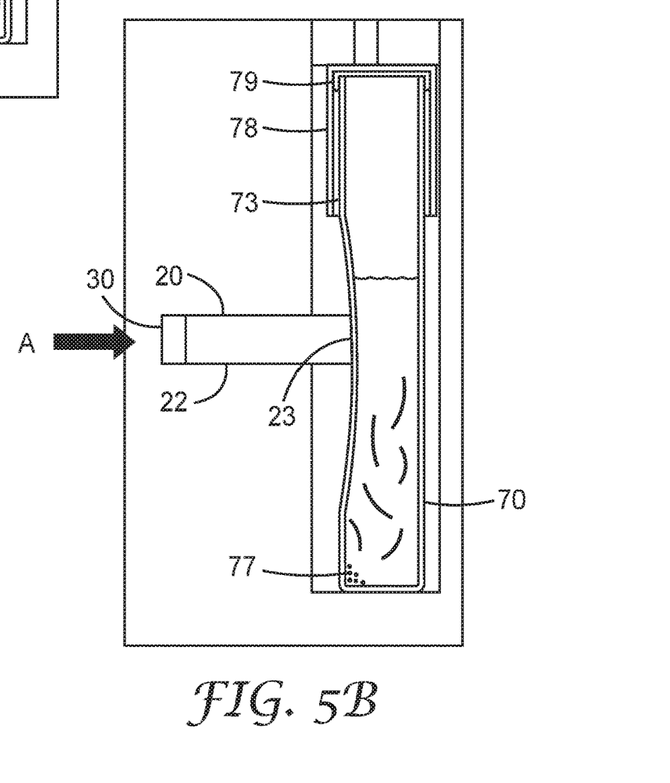

FIGS. 5A-C show sequential cross-sectional side views of an embodiment of an activator system 1000 of the present disclosure as the actuator mechanism activates a biological indicator. The activator system 1000 comprises an activator device 100 as described hereinabove and a biological indicator 70. The biological indicator 70 comprises, for example, a housing having an open cavity defined by at least one wall; a container, which holds detection medium, disposed in the cavity; and a predetermined number of viable sterilization process resistant test microorganisms disposed in the cavity; each component as described hereinabove.

The activator device 100 of the activator system 1000 comprises a receptacle 10 that includes a compartment 12 configured (e.g., shaped and/or dimensioned) to receive the biological indicator 70. The device 100 further comprises an actuator mechanism 20, and a sensing system 30 operatively coupled to the actuator mechanism 20. The actuator mechanism 20 comprises a part (piston 22) as described herein. In some embodiments of the activator system 1000, the receptacle 10 comprises a detachable vented plug 14, which allows sterilant to permeate the receptacle of the activator system, as described herein. In some embodiments, the sensing system 30 is a chemical, such as a wax 32, which expands on heating.

FIG. 5A shows the piston 22 of the actuator mechanism 20 in a first position. The piston 22 has an activating end 23 that is configured to activate the biological indicator 70. In some embodiments, the activating end 23 may comprise a generally-flat surface for contacting the biological indicator 70. Other shapes may be suitable provided they can activate the biological indicator 70 (e.g., by crushing an ampule of medium disposed in the biological indicator) without breaching the housing of the biological indicator 70.

When the piston 22 is disposed in a first position (e.g., as shown in FIG. 5A), the activating end 23 of the piston 22 may be in contact with the at least one wall 73 of the biological indicator. However, in the first position, the piston 22 is not exerting force against the biological indicator 70 (or the container disposed therein) that would be sufficient to activate the biological indicator 70 (e.g., by rupturing the container). Alternatively (not shown), when the piston 22 is disposed in the first position, the activating end 23 of the piston 22 is spaced apart from the biological indicator.

During activation, the actuator mechanism 20 continues to move the activating end 23 of the piston 22 in the direction of arrow A until it causes release of the detection medium 75 from the container 74 (e.g., by fracturing the container as shown in FIG. 5B). Release of the detection medium 75 from the container permits contact between the detection medium 75 and the source of biological activity (e.g., test microorganisms 77). If one or more of the test microorganisms 77 is viable (e.g., after exposure to a sterilant), the test microorganism(s) can react with the detection medium 75 to produce a detectable signal (e.g., color, fluorescence) indicating that exposure to the sterilant did not inactivate the source of biological activity (e.g., kill all of the test microorganisms 77) and, thus, it can be concluded the sterilization process was not efficacious. In contrast, if all of the test microorganisms are killed by the sterilant, the detectable signal is not produced and, thus, it can be concluded the sterilization process was efficacious.

In the illustrated embodiment of FIGS. 5A-B, the part (piston 22) of the actuator mechanism 20 is configured to move from the first position to the second position in a direction that is substantially orthogonal to the longitudinal axis of the compartment 12 of the receptacle 10. In alternative embodiments described herein, the part is configured to move from the first position to the second position in a direction that is substantially along the longitudinal axis.

Figure 6A:
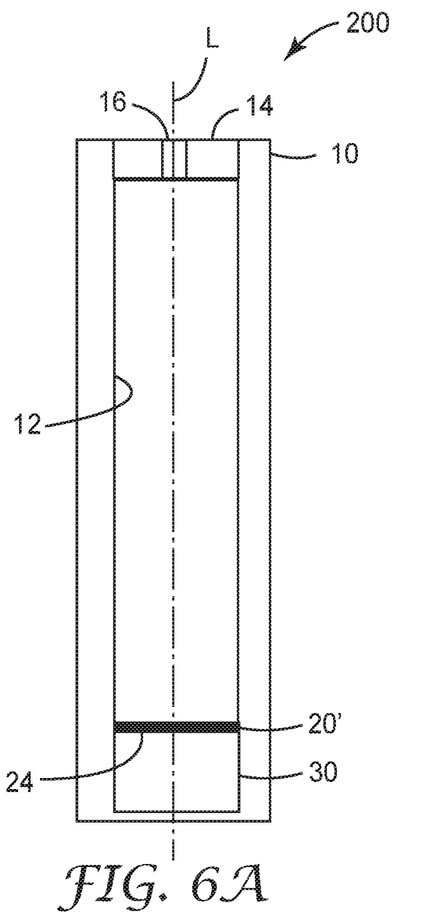
FIG. 6A is a cross-sectional side view of an alternative embodiment of an activator device of this disclosure, wherein the actuator mechanism of the device comprises a deformable septum disposed in a first position.
Figure 6B:
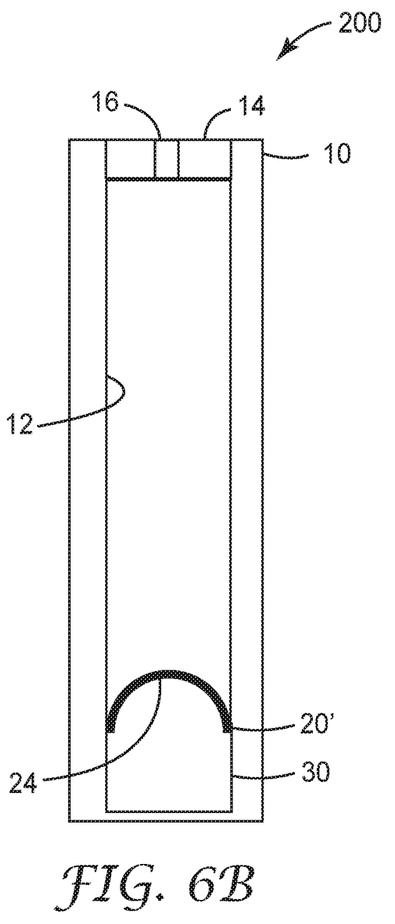
FIG. 6B is a cross-sectional side view of the activator device of FIG. 6A, wherein the deformable septum is disposed in a second position.

In some embodiments, the actuator mechanism of the present disclosure comprises a septum that changes shape in response to expansion of the sensing system to compress and activate the biological indicator. FIGS. 6A-B show one embodiment of an activator device comprising an actuator mechanism that includes a deformable septum. The activator device 200 contains a receptacle 10 for a biological indicator 70, an actuator mechanism 20', and a sensing system 30 operatively coupled to the actuator mechanism 20'. The receptacle 10 comprises a compartment 12 configured (e.g., shaped and/or dimensioned) to receive a biological indicator. The compartment 12 has a longitudinal axis L. The compartment 12 is in fluid communication with the ambient environment (e.g., the atmosphere) outside the receptacle 10. In some embodiments, the activator device 200 further comprises a plug 14. The plug can comprise a vent 16 that allows a sterilant, such as steam, hydrogen peroxide, ethylene oxide, etc., to permeate the compartment 12 of the receptacle 10 and a biological indicator (not shown in FIG. 6A) disposed therein. In some embodiments, the sensing system 30 is a chemical, such as a wax 32, which expands on heating. In some embodiments, the actuator mechanism 20' of the present disclosure comprises a deformable septum 24 that is configured to move from a first position (shown in FIG. 6A) to a second position (shown in FIG. 6B) in response to a force (e.g., a force generated by expansion of a wax 32 as it is heated and changes from a solid to a liquid state). When the deformable septum 24 moves from the first position to the second position, it thereby compresses and activates a biological indicator (not shown in FIGS. 6A-B) disposed in the compartment 12 of the activator device 200. Thus, in some embodiments, the second position of the septum 24 of the actuator mechanism 20' places at least a portion of the deformable septum in a volume defined by the compartment 12 of the receptacle 10.

In the illustrated embodiment of FIGS. 6A-B, the deformable septum 24 of the actuator mechanism 20' is configured to move (e.g., by deformation) from the first position to the second position in a direction that is substantially along the longitudinal axis L of the compartment 12 of the receptacle 10.

Figure 7A:
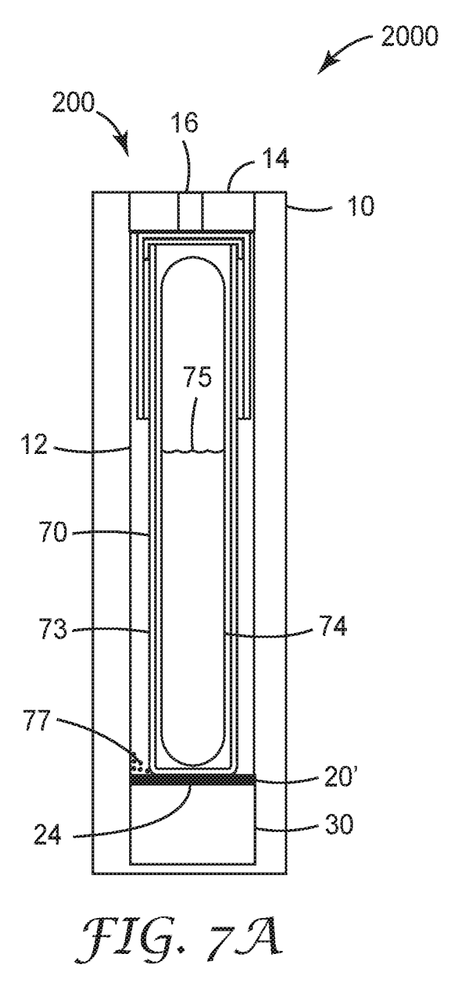
Figure 7B:
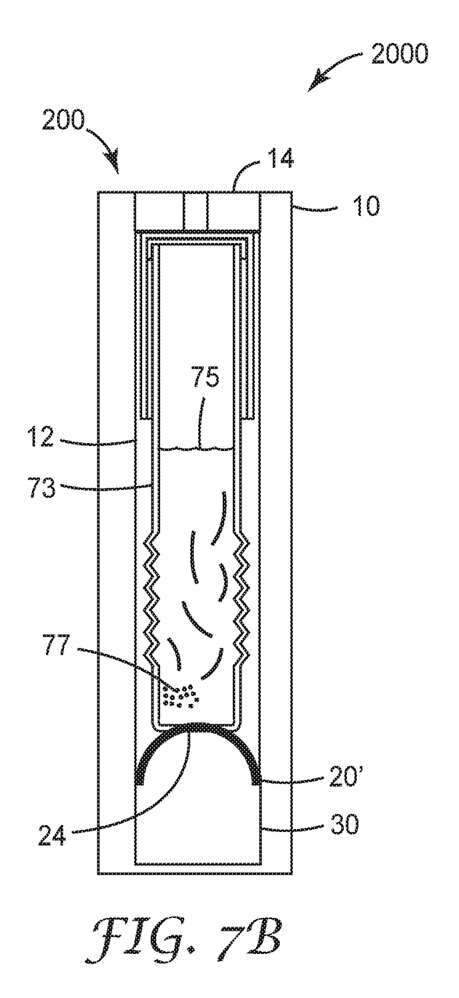

FIGS. 7A-B show sequential cross-sectional side views of an embodiment of an activator system 2000 of the present disclosure as the actuator mechanism activates a biological indicator. The activator system 2000 comprises an activator device 200 as described hereinabove and a biological indicator 70. The biological indicator 70 comprises, for example, a housing having an open cavity defined by at least one wall; a container, which holds detection medium, disposed in the cavity; and a predetermined number of viable sterilization process resistant test microorganisms disposed in the cavity; each component as described hereinabove.

The activator device 200 of the activator system 2000 comprises a receptacle 10 that includes a compartment 12 configured (e.g., shaped and/or dimensioned) to receive the biological indicator 70. The device 200 further comprises an actuator mechanism 20', and a sensing system 30 operatively coupled to the actuator mechanism 20'. The actuator mechanism 20' comprises a deformable septum 24 as described herein. In some embodiments of the activator system 2000, the receptacle 10 comprises a detachable vented plug 14, which allows sterilant to permeate the receptacle of the activator system, as described herein. In some embodiments, the sensing system 30 is a chemical, such as a wax 32, which expands on heating. FIG. 7A shows the septum 24 of the actuator mechanism 20' in a first position.

When the deformable septum 24 is disposed in a first position (e.g., as shown in FIG. 7A), the septum 24 may be in contact with the at least one wall 73 of the biological indicator. However, in the first position, the septum 24 is not exerting force against the biological indicator 70 (or the container 74 holding the detection medium 75 disposed in the biological indicator 70) that would be sufficient to activate the biological indicator 70 (e.g., by rupturing the container 74).

When actuated, the actuator mechanism 20' moves the septum 24 (e.g., by deformation) into the compartment 12. The movement of the septum 24 against the biological indicator 70 exerts pressure against the container 74 that holds the detection medium 75, causing the container 74 to rupture and release the detection medium 75, as shown in FIG. 7B.

Release of the detection medium 75 from the container permits contact between the detection medium 74 and the source of biological activity (e.g., test microorganisms 77). If one or more of the test microorganisms 77 is viable (e.g., after exposure to a sterilant), the test microorganism(s) can react with the detection medium 74 to produce a detectable signal (e.g., color, fluorescence) indicating that exposure to the sterilant did not kill all of the test microorganisms 77 and, thus, it can be concluded the sterilization process was not efficacious. In contrast, if all of the test microorganisms are killed by the sterilant, the detectable signal is not produced and, thus, it can be concluded the sterilization process was efficacious.

Figure 8A:
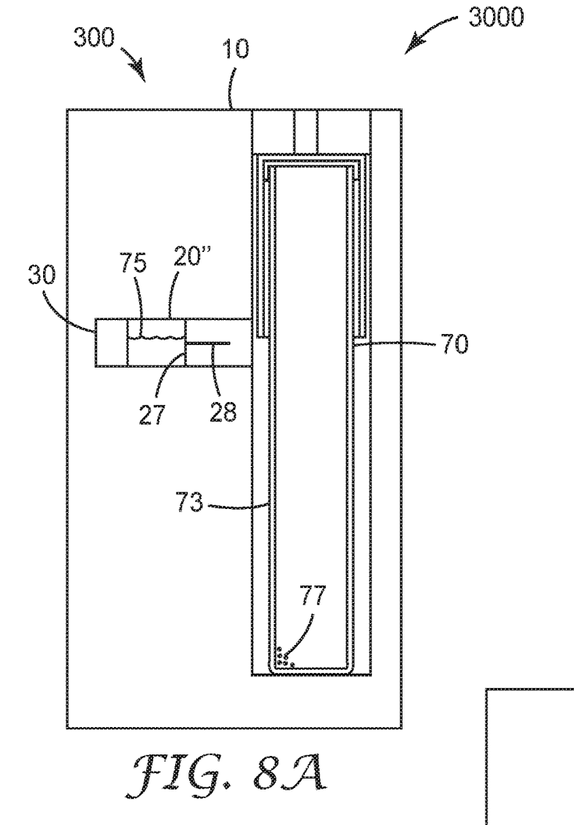
Figure 8B:
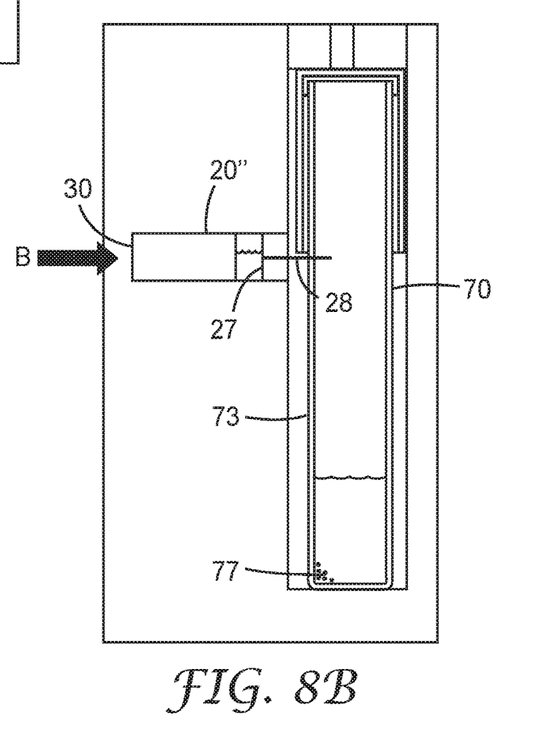

FIGS. 8A-B show an alternative embodiment of an activator system wherein the actuator mechanism contains therein a reagent for detecting a biological activity. The activator system 3000 comprises an activator device 300 and a biological indicator 70. The biological indicator 70 can comprise any biological indicator described herein above with the proviso that, in these embodiments, the container holding the reagent for detecting a biological activity (see container 74 holding detection reagent 75 in FIG. 5A) described above is optional. In the illustrated embodiment of FIG. 8A, the biological indicator 70 includes the test microorganisms 77, but does not include a container holding the detection reagent.

The activator device 300 comprises a receptacle 10 as described hereinabove. The activator device further comprises an actuator mechanism 20" that contains therein contains therein a detection medium 75 comprising a reagent for detecting a biological activity. The reagent for detecting a biological activity can be any detection reagent described herein. The actuator mechanism 20" is configured to deliver the detection medium 75 into the biological indicator 70. By way of example, the actuator mechanism 20" can comprise a syringe-like body 27 with a piercing element 28 capable of piercing the at least one wall of the biological indicator to deliver the detection medium 75 into the biological indicator. The activator device 200 also comprises a sensing system 30 operatively coupled to the actuator mechanism 20" as described herein above.

FIG. 8A shows the activator system 3000 before activation wherein the actuator mechanism 20" is disposed in a first position. FIG. 8B shows the activator system 3000 after activation wherein the piercing element 28 of the actuator mechanism 20" has moved in the direction of arrow B, has pierced the wall 73 of the biological indicator 70 and the actuator mechanism 20" has delivered at least a portion of the detection medium 75 into the biological indicator 70. Delivery of the detection medium 75 into the biological indicator 70 places the source of biological activity (e.g., test microorganisms 70) in contact with the detection medium, thereby permitting detection of any of the source of biological activity that was not inactivated by the sterilization process to which the biological indicator is exposed.

In some embodiments, during use, the biological indicator is placed into the receptacle of the disclosure so that it sits between the top of the actuator mechanism and the bottom of the vented plug in such a manner that the biological indicator is not longitudinally or radially compressed. The activator system, containing the biological indicator, is placed into a sterilizer along with items that are to be sterilized. In some embodiments, during use, particularly in a steam sterilizer, once the sterilization process is begun, the temperature of the sterilizer chamber rises whereupon the temperature of the wax of the sensing system begins to rise. Typically, there is a lag time between start of the steam sterilization process and full, uninterrupted steam exposure; during this lag period, the sterilizer may be alternatively pressurized with steam, and evacuated, to remove non-condensable gases, such as air, from the sterilizer chamber. At the end of this lag period, full, uninterrupted steam exposure occurs. The steam exposure period typically occurs for around 4-5 minutes at temperatures above 132° C. and pressures above 30 PSI, or for around 20 minutes at temperatures above 121° C. and pressures above 20 PSI. During this period of the sterilization process, the biological indicator is subjected to uninterrupted exposure to steam by virtue of steam flowing through the vented plug. During this period of the sterilization process, in some embodiments, the wax of the sensing system melts, but is prevented from expanding due to the pressure inside the receptacle of the activator system that results from pressurized steam entering the receptacle through the vented plug. Typically, after between about 4 and about 20 minutes of full, uninterrupted steam exposure, the sterilizer causes the steam to be removed from the sterilizer chamber using a vacuum, which concomitantly lowers the pressure inside the receptacle of the activator system. The reduced pressure inside the receptacle allows the wax to expand, which, in turn, causes the piston or septum of the actuator to move upward, thus compressing the biological indicator, causing the detection medium-comprising ampoule of the biological indicator to break, and thus activating the biological indicator by allowing the detection medium to contact the source of biological activity (e.g., bacterial spores) of the biological indicator. Without undo experimentation, the wax of the activator system of the present disclosure can be chosen so that the biological indicator is activated within a warm sterilizer chamber, thus providing a ready-to-read biological indicator upon removal of the activator system and, consequently, the biological indicator, from the sterilizer.

As stated previously, the activator system of the present disclosure comprises a receptacle, a sensing system, and an actuator mechanism. In certain embodiments of the activator system or activator device, the sensing system is capable of sensing a parameter selected from the group consisting of pressure, temperature, time, and a combination of any two or more of the foregoing parameters. The sensing system may be an implicit sensing system or an explicit sensing system. Implicit sensing systems respond to, and thus implicitly sense, changes in temperature and pressure. In certain embodiments of the activator system or activator device, the sensing system comprises a temperature-responsive chemical. An example of an implicit sensing system is a solid, liquid, or gas that responds to a change in temperature by expanding or contracting. Some liquids, for example, some silicone oils, expand dramatically upon heating and thus are implicit temperature sensors. More particularly, some implicit sensing systems expand most dramatically during a phase change. In certain embodiments of the activator system or activator device, the temperature-reactive chemical has a first density when in a solid state and a second density when in a liquid state, wherein the first density is higher than the second density. For example, a wax that has a melting point below about 100° C. or a melting point that is greater than about 100° C. may serve as a sensing system for the activating system of this disclosure because it melts, and expands, at temperatures below that which are achieved during a steam sterilization process. The sensing system may be an explicit sensing system. Explicit sensing systems used in the activator system of the disclosure determine the temperature and/or pressure of the sterilizer chamber and/or the time that the sterilization process has progressed. For example, a thermistor may be used in the activating system of the disclosure to measure the temperature of the sterilizer chamber, the result of which can be provided via an electrical signal to the actuator mechanism to activate the biological indicator.

As discussed previously, the activator system of the disclosure comprises a receptacle. The receptacle holds the biological indicator and typically comprises a roughly cylindrically shaped lumen with sides, a bottom, and a top. In some embodiments, the top of the lumen is formed by lowering (e.g., by rotating) a threaded vented plug though a threaded portion of the receptacle so that the bottom of the vented plug just touches the top of a biological indicator without compressing the biological indicator. The bottom of the receptacle, in some embodiments, is formed by the top of a piston, which, itself, is the actuator mechanism of the disclosure. In some embodiments, the receptacle, except by virtue of the vented plug, is impermeable to sterilant, while in other embodiments the receptacle is permeable to sterilant. For example, the receptacle may comprise a lumen that has been cut away or drilled out of a solid piece of metal or plastic, the sides of which are impermeable to sterilant. Alternatively, the receptacle may be permeable to sterilant. For example, the receptacle may comprise a perforated chamber, such as can be formed from a piece of plastic that is perforated with holes formed by cutting away or drilling out material from which the receptacle is fashioned. Preferably, for activator systems of the present disclosure that employ implicit sensing systems, the receptacle is impermeable to sterilant. Preferably, for activator systems of the present disclosure that employ receptacles that are process challenge devices, the receptacle is impermeable to sterilant.

As stated previously, in some embodiments, the receptacle of the activator system of the disclosure comprises a vented plug. The vented plug is vented by a lumen that passes through the vented plug so that the biological indicator is allowed to be in fluid communication with sterilant during use of the activator system in a sterilizer. The lumen of the vented plug may be made to have any convenient dimensions. In some embodiments, however, wherein the receptacle of the activator system is a process challenge device, the lumen of the vented plug should limit the ingress of sterilant into the receptacle from the sterilizer.

As stated previously, the activator system of the present disclosure comprises an actuator mechanism, which moves in response to the sensing system of the activator system to accomplish activation of the biological indicator. In some embodiments, the actuator mechanism comprises a piston that moves longitudinally to compress the biological indicator along its long axis; the movement of the piston causes a detection medium-comprising vial of the biological indicator to break, thus allowing detection medium to combine with the source of biological activity (e.g., bacterial spores). In some embodiments, the actuator mechanism of the disclosure comprises a deformable septum, such as a rubber septum, which expands and results in compression of the biological indicator longitudinally or radially (i.e., perpendicular to the long axis of the biological indicator); the expansion of the septum causes a detection medium-comprising vial of the biological indicator to break, thus allowing detection medium to combine with the source of biological activity (e.g., bacterial spores) (activation). In some embodiments, the actuator mechanism of the disclosure comprises a septum, such as a rubber septum, and a piston, the combination of which results in compression of the biological indicator radially or longitudinally; the expansion of the septum acting on the piston causes a detection medium-comprising vial of the biological indicator to break, thus allowing detection medium to combine with the source of biological activity (e.g., bacterial spores). The actuator mechanism may comprise a mechanical actuator, an electrical actuator, a chemical actuator, or a combination thereof.

In some embodiments, the actuator mechanism comprises a mechanical actuator. Examples of mechanical actuators are substances and materials that expand or change shape on heating. For example. a metal that changes shape in response to a message from the sensing system is a mechanical actuator; the change in shape of the metal causes a detection medium-comprising vial of the biological indicator to break, thus allowing detection medium to combine with the source of biological activity (e.g., bacterial spores). In some embodiments, the mechanical actuator is also the sensing system. For example, a material, such as a metal, can act as the sensing system by responding to heating by changing shape and expanding, and it can act as a mechanical actuator of the actuator mechanism by compressing the biological indicator longitudinally or radially. Other materials that can act as mechanical actuators include waxes and liquids, such as silicone oils, that expand on heating; these materials can also serve simultaneously as the sensing system in the present disclosure. In some embodiments of the activator system or the activator device, the actuator mechanism comprises a mechanical actuator, wherein at least a portion of the mechanical actuator changes from a first physical state to a second physical state in response to a temperature between 100° C. and 134° C. In these embodiments, the portion (e.g., an oil or a wax) has a higher density when it is in the first physical state than its corresponding density in the second physical state.

In certain embodiments of the activator system or activator device, the sensing system comprises a receiver that receives data from a sterilizer.

In some embodiments, the actuator mechanism comprises an electrical actuator. An example of an electrical actuator is a direct current electrical motor powered by a hermetically sealed battery capable of operation at high temperatures and pressures. The motor can be switched from an "off" state to an "on" state and subsequently move a piston or a septum in response to a message from the sensing system; the movement of the piston or the septum causes a detection medium-comprising vial of the biological indicator to break, thus allowing detection medium to combine with the source of biological activity (e.g., bacterial spores). The motor may be coupled to a piston by a lead screw. The lead screw is chosen to have a screw pitch and a length to allow a precise vertical movement of the piston connected to the lead screw. The extent of the vertical movement is controlled by the length of time that the motor is run at a given speed (rotations per minute).

In those embodiments, the direct current motor is chosen to withstand temperatures higher than 150 C and to achieve the desired rotational speed at the appropriate torque force, for a given applied current at the motor's rated voltage. The motor may have an integrated gear box to achieve the desired rotational speed and torque force. To control the operation of the motor during a sterilization cycle, the sensing system, comprising a thermistor or a similarly suitable temperature probe or thermocouple, and/or a pressure sensor, senses the appropriate condition of time, temperature, and/or pressure and provides a signal to switch the motor to the "on" state for a predetermined time.

Various methods and devices may be used to provide the signal to the motor to switch it to the on- or off state; for example, a logic circuit design with an integrated digital clocking system may be incorporated into the electrical actuator mechanism. Furthermore, various conditions may be desired during which the motor of the electrical actuator system is switched from the off to the on state. For example, the motor may be desired to be switched to the on state when the sterilization chamber temperature is 134° C. and the pressure is above 2.5 bars absolute for 4 minutes. Alternatively, the motor may be desired to be switched to the on state when the pressure in the sterilization chamber drops from a reading greater than 2.5 bars absolute to sub atmospheric pressure and the temperature is less than 120° C.

Many possible logic criteria may be used to switch the motor to the on and off states, including combinations of one or more of the measured parameters (time, temperature and pressure), using either absolute setpoints or differential conditions as well as combinations thereof may be used. Optionally, the logic circuit may include a memory storage bank to log time, temperature and pressure data during the sterilization cycle.

In some embodiments, the actuator mechanism comprises a chemical actuator. An example of a chemical actuator is a material that comprises one or more chemical compounds that expand on reaction or decomposition in response to a message from the sensing system; the expansion of the material activates the biological indicator; the expansion of the material moves the piston or the septum of the actuator mechanism and causes a detection medium-comprising vial of the biological indicator to break, thus allowing detection medium to combine with the source of biological activity (e.g., bacterial spores). In some embodiments, the chemical actuator is also the sensing system. Examples of chemicals that decompose on heating to generate a gas are β-ketoacids or dicarboxylic acids, which decompose on heating to produce carbon dioxide.

In some embodiments, the actuator mechanism is a combination of one or more actuators.

In some embodiments, the actuator mechanism and the sensing system have commonalities. For example, when a wax is used as the sensing system of the activator system of the disclosure, it may also act as a mechanical actuator of the activator system, because the expansion of the wax that results from melting of the wax in response to changes in conditions within the sterilizer chamber acts to move a piston or septum of the actuator mechanism so that activation of the biological indicator occurs.

In another aspect, the present disclosure provides a method of determining efficacy of a sterilization process. The method comprises placing a device into a sterilization chamber of a sterilizer. The device can be any embodiment of the actuator device described herein. The device comprises a receptacle that defines a compartment dimensioned to receive a biological indicator, an actuator mechanism, and a sensing system operatively coupled to the actuator mechanism, each component as disclosed herein. A biological indicator as disclosed herein is disposed in the compartment of the receptacle. A source of biological activity as disclosed herein is disposed in the biological indicator. The sterilizer can be any sterilizer comprising a sterilization chamber in which articles can be exposed to a sterilization process that uses a gaseous sterilant such as steam, ethylene oxide or hydrogen peroxide, for example.

The method further comprises sealing the sterilization chamber (e.g., so that proper sterilization conditions such as temperature, pressure, humidity, and/or sterilant concentration, for example, can be maintained during the sterilization process. After sealing the sterilization chamber, the method comprises exposing the device and the biological indicator to a sterilant (e.g., steam, ethylene oxide or hydrogen peroxide) in the sterilization chamber. In some implementations of the method, exposing the device and the biological indicator to a sterilant may comprise exposing the device and the biological indicator to a sterilant under conditions (e.g., time, temperature, pressure, humidity, etc.) intended to sterilize the device, the biological indicator and, optionally, an article disposed in the sterilization chamber with the device and the biological indicator.

During or after the exposing the device and the biological indicator to the sterilant, but before unsealing the sterilization chamber, the method further comprises activating the biological indicator while the biological indicator is disposed in the sterilization chamber. Activating the biological indicator comprises contacting the source of biological activity with a detection reagent to form a mixture. The detection reagent is capable of being changed from a first state to a second state directly or indirectly by the biological activity, as disclosed herein.

After activating the biological indicator, the method further comprises analyzing the biological indicator to detect a presence or absence of the second state of the detection reagent in the mixture. The second state can be detected by means that are well known in the art including, but not limited to, visual detection, spectrophotometric detection, fluorometric detection, and chemiluminescent detection. In any implementation of the method, detecting the presence or absence of the second state of the detection reagent further comprises measuring a quantity of the second state of the detection reagent. In any implementation of the method, measuring a quantity of the second state of the detection reagent further comprises comparing the measured quantity of the second state of the detection reagent to a reference value in order to determine whether the sterilization process was efficacious.

According to the method of the present disclosure, in some implementations of the method, activating the biological indicator comprises contacting a portion of the biological indicator with the actuator mechanism (e.g., contacting the biological indicator with a piston, as described hereinabove). In certain implementations of the method, activating the biological indicator comprises opening the sealed reservoir (e.g., by fracturing a frangible ampoule, as described hereinabove).

In any implementation of the method, contacting the source of biological activity with a detection reagent is implemented by the actuator mechanism. For example, a portion (e.g., a piston or a septum, as described herein) of the actuator mechanism can be used to open a sealed reservoir (e.g., containing the detection reagent) disposed in the biological indicator. Opening the sealed reservoir releases the detection reagent, thereby permitting it to contact a source of biological activity also disposed in the biological indicator.

In any implementation of the method, contacting the source of biological activity with a detection reagent comprises moving a part (e.g., a piston or a septum) of the actuator mechanism from a first position to a second position, as described hereinabove.

In any implementation of the method, activating the biological indicator while the biological indicator is in the sterilization chamber comprises the sensing system sensing a parameter in the sterilization chamber, wherein the parameter is selected from the group consisting of pressure, temperature, time, and a combination of any two or more of the foregoing parameters.

In any implementation of the method, the activating the biological indicator occurs while a temperature inside the sterilization chamber is higher than 50° C., higher than 60° C., higher than 70° C., higher than 80° C., higher than 90° C., higher than 100° C., higher than 110° C., or higher than 120° C.

EXAMPLES

Example 1

Preparation of Activator System and Demonstration of Decrease of Volume of Receptacle During Post-Exposure Phase of a Steam Sterilization Cycle An activator system was prepared by drilling into one end of a 15 cm-length×7.7 cm-diameter cylindrical piece of poly(tetrafluoroethylene) a 1.5 cm-diameter×12 cm deep hole. Threads were cut into the hole to match those on a steel vented plug (1.5 cm-diameter×1.5 cm-length). Into the other end of the cylindrical piece of poly(tetrafluoroethylene) was cut a 3 cm-diameter×3.2 cm deep hole, that connected with the hole that was drilled from the other end. To separate the two holes, and to make an expandable chamber, a circular piece of silicone rubber (the nascent septum) was placed at the junction of the two holes and secured in place with an aluminum gasket and screws. Next, into the 3 cm-diameter× 3.2 cm deep hole was poured molten wax with a phase change temperature of 60° C. (PlusICE PCM A60, available from PCM Products, Limited, Cambridgeshire, UK). After the wax solidified, an aluminum cover was screwed into place over the wax-containing hole using six 3 cm-length screws. The nascent activator system was then fitted, through the other, open end of the receptacle, with a poly (tetrafluoroethylene) piston.

The activator system, thus prepared, was placed (wax-containing end down) into a sterilizer that was programmed for a pre-vacuum steam sterilization cycle. Prior to beginning the sterilization cycle, a measuring stick was placed into the top, open end of the activating system. During the sterilization cycle, the measuring stick was observed, through a viewing window of the sterilizer, to remain in place until the pressure in the sterilizer chamber dropped during the post-exposure, vacuum drying stage of the sterilization cycle, during which the measuring stick was seen to rise. The results of the experiment showed that the receptacle volume decreased, as the pressure in the sterilization chamber decreased, due to expansion of the wax and the concomitant expansion of the septum and movement of the piston. The results showed, moreover, that the receptacle volume did not decrease during the pre-vac or exposure phase of the cycle.

Example 2

Activation of a Biological Indicator During Post-Exposure Phase of a Steam Sterilization Cycle Using a Mechanical Activator An activator system was prepared as in example 1. Instead of placing a measuring stick into the open end of the receptacle, however, a biological indicator (Super Rapid Steam Biological Indicator, 1492V available from 3M, St. Paul, Minnesota) was placed into the receptacle with the cap of the biological indicator directed toward the top, open end of the receptacle. Then, the vented plug from example 1 was screwed into place so that the bottom of the vented plug touched, but did not depress, the cap of the biological indicator. (The distance into the receptacle that the vented plug was placed so that the cap was not depressed was determined and recorded in previous trial-and-error experiments.) The activator system was then placed into a sterilizer that was programmed for a pre-vacuum steam sterilization cycle. After completion of the sterilization cycle, the activator system was removed from the sterilizer, the vented plug was removed from the receptacle, and the biological indicator was removed from the receptacle. An observation of the biological indicator showed that it had been activated. The results of the experiment showed that a biological indicator can be activated and incubated within a closed sterilizer.

Prophetic Example 3

Activation of a Biological Indicator During Post-Exposure Phase of a Steam Sterilization Cycle Using a Mechanical Activator An activator system is prepared as in example 2, except that instead of placing a wax into the hole in the bottom of the receptacle, no wax is used, and a piece of flexible metal replaces the septum that is screwed into place below the piston. The activator system is then placed into a sterilizer that is programmed for a pre-vacuum steam sterilization cycle. After completion of the sterilization cycle, the activator system is removed from the sterilizer, the vented plug is removed from the receptacle, and the activated biological indicator is removed from the receptacle. An observation of the biological indicator shows that it has been activated.

Prophetic Example 4

Activation of a Biological Indicator During Post-Exposure Phase of a Steam Sterilization Cycle Using a Chemical Activator An activator system is prepared as in example 2, except that a 99:1 mixture of maleic anhydride and water is placed into the hole in the bottom of the receptacle. The activator system is then placed into a sterilizer that is programmed for a pre-vacuum steam sterilization cycle. After completion of the sterilization cycle, the activator system is removed from the sterilizer, the vented plug is removed from the receptacle, and the activated biological indicator is removed from the receptacle. An observation of the biological indicator shows that it has been activated.

Prophetic Example 5

Activation of a Biological Indicator During Post-Exposure Phase of a Steam Sterilization Cycle Using an Electrical Activator An activator system is prepared by drilling into the first end of a 15 cm-length×7.7 cm-diameter cylindrical piece of poly(tetrafluoroethylene) a 1.5 cm-diameter×12 cm deep bore. Threads are cut into the bore to match those on a steel vented plug (1.5 cm-diameter×1.5 cm-length). A bore, sufficiently large to house a direct current motor and connected with the bore drilled from the first end of the cylindrical piece of poly(tetrafluoroethylene), is cut into the second end of the cylindrical piece of poly(tetrafluoroethylene). The direct current motor is mechanically coupled to a lead screw which in turn is mechanically coupled to a poly(tetrafluoroethylene) piston. The piston is sized to ride in the 1.5 cm bore drilled into the first end of the poly(tetrafluoroethylene) cylinder.

A biological indicator (Super Rapid Steam Biological Indicator, 1492V available from 3M, St. Paul, Minnesota) is placed into the 1.5 cm bore drilled into the first end of the poly(tetrafluoroethylene) cylinder, with the cap of the biological indicator directed toward the open end of the bore. Then, the vented steel plug (1.5 cm-diameter×1.5 cm-length) is screwed into the open end of the 1.5 cm bore so that the bottom of the vented plug touches, but does not depress, the cap of the biological indicator. (The distance into the receptacle that the vented plug is placed so that the cap is not depressed is determined and recorded in previous trial-and-error experiments.) The activator system, thus prepared, is placed into a sterilizer that is programmed for a pre-vacuum steam sterilization cycle. During operation, when the appropriate pre-defined logic criteria for switching the motor to the on state are achieved in the sterilization chamber, the motor runs for a pre-determined amount of time at a defined rotational speed, causing a vertical displacement of the poly(tetrafluoroethylene) piston which, in turn, results in depressing the biological indicator's cap against the steel vented plug by an amount sufficient to activate the biological indicator. After completion of the sterilization cycle, the activator system is removed from the sterilizer, the vented plug is removed from the receptacle, and the biological indicator is removed from the receptacle. An observation of the biological indicator shows that it has been activated.

We claim:

1. A device for assessing efficacy of a sterilization process, comprising:
    a biological indicator;
    a receptacle configured to receive the biological indicator;
    an actuator mechanism disposed within the system and adjacent to the receptacle; and
    a sensing system configured to sense conditions of the sterilization process, wherein the sensing system senses a parameter selected from the group consisting of pressure, temperature, time, and a combination thereof of the sterilization process during exposure of the device to the sterilization process.

2. The device of claim 1, wherein the biological indicator comprises a source of biological activity disposed therein.

3. The device of claim 1, wherein the biological indicator comprises a sealed reservoir.

4. The device of claim 1, wherein the actuator mechanism comprises a part that is configured to move from a first position to a second position.

5. The device ystem of claim 1;
    wherein the receptacle comprises a compartment configured to hold the biological indicator;
    wherein the compartment defines a volume;
    wherein the second position is located within the volume.

6. The device of claim 1, wherein the sensing system comprises a temperature-responsive chemical.

7. The device of claim 6, wherein the temperature-responsive chemical has a first density when in a solid state and a second density when in a liquid state, wherein the first density is higher than the second density.

8. The device of claim 1, wherein the sensing system is electrically or electronically connected to a sterilizer.

9. The device of claim 1, wherein the actuator mechanism comprises at least one actuator chosen from a mechanical actuator, an electrical actuator, a chemical actuator, or a combination thereof.

10. The device of claim 1, wherein the actuator mechanism comprises a mechanical actuator, wherein at least a portion of the mechanical actuator changes from a first physical state to a second physical state in response to a temperature between 100° C. and 134° C.

11. The device of claim 10, wherein the portion has a higher density in the first physical state than in the second physical state.

12. The device of claim 10, wherein the mechanical actuator comprises a wax.

13. The device of claim 1, wherein the sensing system comprises a receiver that receives data from a sterilizer.

14. A device, comprising:
    a receptacle configured to receive a biological indicator;
    an actuator mechanism disposed within the device and adjacent to the receptacle; and
    a sensing system configured to sense conditions of a sterilization process, wherein the sensing system is operatively coupled to the actuator mechanism, wherein the sensing system senses a parameter selected from the group consisting of pressure, temperature, time, and a combination thereof of the sterilization process during exposure of the device to the sterilization process.

15. A device for assessing efficacy of a sterilization process, comprising:
    a biological indicator;
    a receptacle configured to receive the biological indicator;
    an actuator mechanism disposed within the system and adjacent to the receptacle; and
    a sensing system configured to sense conditions of the sterilization process during exposure of the device to the sterilization process, wherein the sensing system is operatively coupled to the actuator mechanism, and the sensing system comprises a temperature-responsive chemical.

16. A device for assessing efficacy of a sterilization process, comprising:
    a biological indicator;
    a receptacle configured to receive the biological indicator;
    an actuator mechanism disposed within the system and adjacent to the receptacle, wherein the actuator mechanism comprises a mechanical actuator, and at least a portion of the mechanical actuator changes from a first physical state to a second physical state in response to a temperature between 100° C. and 134° C.; and a sensing system configured to sense conditions of the sterilization process during exposure of the device to the sterilization process, wherein the sensing system is operatively coupled to the actuator mechanism.

* * * * *